(12) United States Patent
Robinson et al.

(10) Patent No.: US 11,608,495 B2
(45) Date of Patent: Mar. 21, 2023

(54) BIODEGRADABLE POLYESTER-BASED POLYURETHANE FOAMS

(71) Applicant: EVOCO LTD., Toronto (CA)

(72) Inventors: Jason James Robinson, Toronto (CA); Natalie Beth Ashdown, Toronto (CA); Gregory Allan Whitton, Etobicoke (CA)

(73) Assignee: EVOCO LTD., Toronto (CA)

( * ) Notice: Subject to any disclaimer, the term of this patent is extended or adjusted under 35 U.S.C. 154(b) by 0 days.

(21) Appl. No.: 17/546,433

(22) Filed: Dec. 9, 2021

(65) Prior Publication Data

US 2022/0098571 A1 Mar. 31, 2022

Related U.S. Application Data

(63) Continuation of application No. PCT/CA2020/051640, filed on Nov. 30, 2020.

(60) Provisional application No. 62/941,980, filed on Nov. 29, 2019.

(51) Int. Cl.
| | | |
|---|---|---|
| *C08G 18/42* | (2006.01) | |
| *C12N 11/093* | (2020.01) | |
| *C08G 18/76* | (2006.01) | |
| *C12N 11/04* | (2006.01) | |
| *C08G 101/00* | (2006.01) | |

(52) U.S. Cl.
CPC ........ *C12N 11/093* (2020.01); *C08G 18/4238* (2013.01); *C08G 18/7671* (2013.01); *C12N 11/04* (2013.01); *C08G 2101/00* (2013.01); *C08G 2110/005* (2021.01); *C08G 2110/0008* (2021.01); *C08G 2110/0058* (2021.01); *C08G 2110/0066* (2021.01)

(58) Field of Classification Search
CPC .... C08G 18/18; C08G 18/22; C08G 18/4238; C08G 18/6633; C08G 18/7671; C08G 2101/00; C08G 2110/0008; C08G 2110/0041; C08G 2110/005; C08G 2110/0058; C08G 2110/0066; C08G 2110/0083; C08G 2230/00; C08K 11/00; C08L 75/06; C08L 101/16; C12N 1/20; C12N 11/04; C12N 11/08; C12N 11/093; C12N 11/098; C12N 11/14; C12R 2001/07

See application file for complete search history.

(56) References Cited

FOREIGN PATENT DOCUMENTS

| CN | 103114084 | * | 4/2015 | |
|---|---|---|---|---|
| CN | 105385707 | * | 3/2016 | |
| CN | 108503793 | * | 9/2018 | |
| FR | 2840310 A1 | * | 12/2003 | ............. C08G 18/12 |

OTHER PUBLICATIONS

Bang, SS et al., "Calcite precipitation induced by polyurethane-immobilized Bacillus pasteurii", Enzyme Microb Technol., Mar. 8, 2001 (Aug. 3, 2001), vol. 28, pp. 404-409, ISSN: 0141-0229.
Cregut, M et al., "New insights into polyurethane biodegradation and realistic prospects for the development of a sustainable waste recycling process", Biotechnol Adv., Dec. 2013 (Dec. 2013), vol. 31, pp. 1634-1647, ISSN: 0734-9750.
The International Search Report from PCT/CA2020/051640 dated Mar. 16, 2021.

* cited by examiner

*Primary Examiner* — John M Cooney

(74) *Attorney, Agent, or Firm* — Hill & Schumacher

(57) ABSTRACT

A biodegradable foam which includes a poly-ester-based polyurethane foam and a mixture comprised of a soil-dwelling carbon-digesting bacteria embedded in a carrier compound. The mixture of the soil-dwelling carbon-digesting bacteria is homogenously dispersed throughout the poly-ester-based polyurethane foam. This biodegradable foam exhibits biodegradation rates higher than a polyester-based polyurethane foam absent the soil-dwelling carbon-digesting bacteria.

33 Claims, 3 Drawing Sheets

BIODEGRADABLE POLYESTER-BASED POLYURETHANE FOAMS

FIELD

The present disclosure relates to biodegradable polyester-based polyurethane foams and methods of producing same.

BACKGROUND

Polyurethane (PU) foams are used in many commercial applications such as footwear, automotive cushioning, mattresses, and many other commercial products. PU foams have a very slow rate of biodegradation with preliminary studies suggesting it would take up to 1000 years to fully degrade under typical landfill conditions. Improving the biodegradation of the PU foam will reduce the material impact on the environment, as the material will spend less time in a landfill.

Biodegradation rates of polyurethanes depend on their structure and more specifically the type of polyol used, with polyester-based PU foams biodegrading at a faster rate than polyether-based PU foams, due to the presence of ester-bonds. However, the presence of ester bonds alone may not lead to appreciable biodegradation of the PU foam within a desired time frame, for example, within 20 years. Additionally, ester bonds play a significant role in the physical and mechanical properties of a foam, where it may not always be desirable or possible to introduce more ester bonds to a PU foam.

Thus, it would be very desirable to provide a method of manufacturing PU foam that can help control the rate of biodegradation of a PU foam in a desired period of time while simultaneously allowing control of the environmental conditions under which the foam is susceptible to biodegradation, while at the same time not compromising the physical or mechanical properties of the foam during its intended product life.

SUMMARY

Disclosed herein is a biodegradable foam which comprises a polyester-based polyurethane foam and a soil-dwelling carbon-digesting bacteria, or a mixture comprised of a soil-dwelling carbon-digesting bacteria embedded in a carrier compound. The mixture of the soil-dwelling carbon-digesting bacteria is substantially homogenously dispersed throughout the polyester-based polyurethane foam. This bacteria-containing polyester polyurethane foam is characterized in that it exhibits tunable biodegradation rates which are higher than a polyester-based polyurethane foam absent the soil-dwelling carbon-digesting bacteria.

The soil-dwelling carbon-digesting bacteria may comprise at least one strain of the genus *Bacillus*.

The soil-dwelling carbon-digesting bacteria may be selected from the group consisting of *Bacillus subtilis, Bacillus pumilus, Bacillus licheniformis, Bacillus megaterium, Bacillus Cerus, Bacillus Alvei, Bacillus coagulans, Bacillus simplex, Bacillus brevis*, and *Bacillus amyloliquefaciens*.

The carrier compound may be selected from the group consisting of Calcium carbonate, Sodium Bicarbonate and Zeolite.

The soil-dwelling carbon-digesting bacteria may be present in the carrier compound, in a range from about 0.001 wt % to about 100 wt %.

The soil-dwelling carbon-digesting bacteria embedded in a carrier compound may be present in the polyester-based polyurethane foam, in a range from about 0.0001 wt % to about 10.0 wt % of the total foam.

The soil-dwelling carbon-digesting bacteria embedded in a carrier compound may be present in the polyester-based polyurethane foam, in a range from about 0.01 to about 0.5 wt % of the total foam.

The biodegradable foam may exhibit a tensile modulus in a range from about 5.0 kg/cm$^2$ to about 100 kg/cm$^2$.

The biodegradable foam may exhibit a density in a range from about 5 kg/m$^3$ to about 1000 kg/m$^3$.

The biodegradable foam may be characterized by an elongation at break in a range from about 15 to about 700%.

The biodegradable foam may have a percent modern carbon in a range from about 0 to about 100%

The biodegradable foam may have a modulus equal to or greater than 50 kg/cm$^2$.

The present disclosure also provides a method of producing a biodegradable polyurethane foam, comprising:

a) mixing polyester polyol with catalysts, water and soil-dwelling carbon-digesting bacteria which may or may not be embedded in a carrier compound, to produce a mixture, and b) mixing isocyanate into said mixture to induce a chemical reaction between the isocyanate and said water to produce carbon dioxide gas, and simultaneously induce a chemical reaction between the isocyanate and said polyester polyol to produce a polyester based polyurethane polymer with carbon dioxide bubbles trapped within to produce said biodegradable polyurethane foam, said biodegradable polyurethane foam characterized in that it exhibits tunable biodegradation rates which are higher than a polyester-based polyurethane foam absent the bacteria.

The method may further comprise adding one or more catalysts to the mixture, the catalyst being selected to catalyze the reaction between isocyanate and water and simultaneously between isocyanate and polyester polyol.

The isocyanate may be selected from the group consisting of 4,4'-Methylene diphenyl diisocyanate, 2,4-Methylene diphenyl diisocyanate, 2,2'-Methylene diphenyl diisocyanate, 2,4-Toluene diisocyanate, 2,6-Toluene diisocyanate, polymeric methylene diphenyl diisocyanate, and carbodiimide-modified methylene diphenyl diisocyanate.

The catalyst may be a tertiary amine catalyst.

The catalyst may be selected from the group consisting of triethylenediamine, N-methylmorpholine, N-methylimidazole, bis(dimethylaminopropyl)amine, dimethylaminoethoxyethanol, Bis-(2-diemthylaminoethyl)-ether, dimethylaminopropylurea, N-dimethylaminopropyl-N-(2-hydroxyethyl)-N-methylamine, and N-dimethylaminoethyl-N-(2-hydroxyethyl)-N-methylamine, dibutyltin dilaurate, Tin(II) 2-ethylhexanoate bismuth neodecanoate, potassium octoate, potassium acetate, zinc carboxylates, and nickel carboxylates.

The soil-dwelling carbon-digesting bacteria may comprise at least one strain of the genus *Bacillus*.

The soil-dwelling carbon-digesting bacteria may be selected from the group consisting of *Bacillus subtilis, Bacillus pumilus, Bacillus licheniformis, Bacillus megaterium, Bacillus cerus, Bacillus alvei, Bacillus coagulans, Bacillus simplex, Bacillus brevis*, and *Bacillus amyloliquefaciens*.

The carrier compound may be selected from the group consisting of calcium carbonate, zeolite, and sodium bicarbonate.

The method may further include mixing into the mixture surfactants, plasticizers and chain extenders.

The method may further include mixing into the mixture flame retardants, anti-oxidants, cell openers, emulsifiers, hardening agents, non-functional fillers, cross-linking agents, dyes, pigments, or other hydroxy or amine functionalized materials.

The soil-dwelling carbon-digesting bacteria embedded in a carrier compound may be present in the mixture in a range from about 0.001 to about 10.0 wt % of the total foam.

The biodegradable polyurethane foam may have an isocyanate index in a range from about 70 to about 200.

The biodegradable polyurethane foam may have an average isocyanate functionality in a range from about 2.0 to about 6.0.

The biodegradable polyurethane foam is characterized by having a polyester polyol molecular weight in a range from about 500 to about 5000 g/mol.

The biodegradable polyurethane foam may have a polyester polyol average hydroxyl functionality in a range from about 1.1 to about 6.0.

The biodegradable polyurethane foam may have a polyester polyol hydroxyl number in a range from about 20 to about 300 mg KOH/g polyol.

A further understanding of the functional and advantageous aspects of the disclosure can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Figure 1:
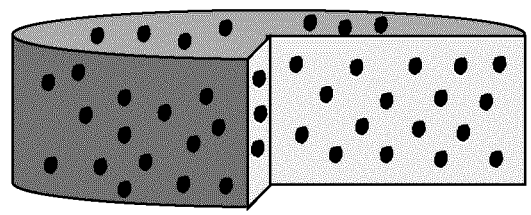
FIG. 1 shows a conceptual drawing of a foam block with embedded bacteria homogenously dispersed throughout the foam.
Figure 2A:
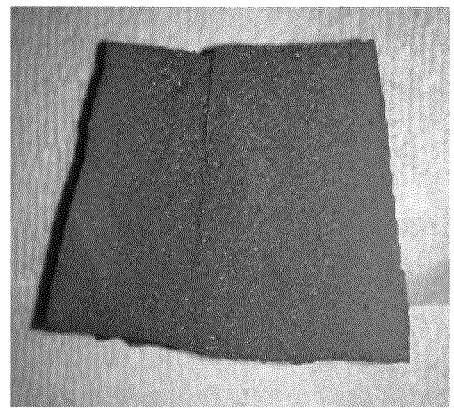
FIGS. 2A, 2B, 2C and 2D show photos of foam from disintegration testing before (2A) and after an aerobic composting test (ISO 16929) (2B, 2C and 2D).
Figure 2B:
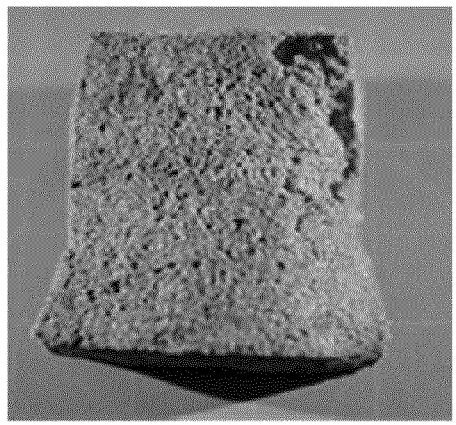
Figure 2C:
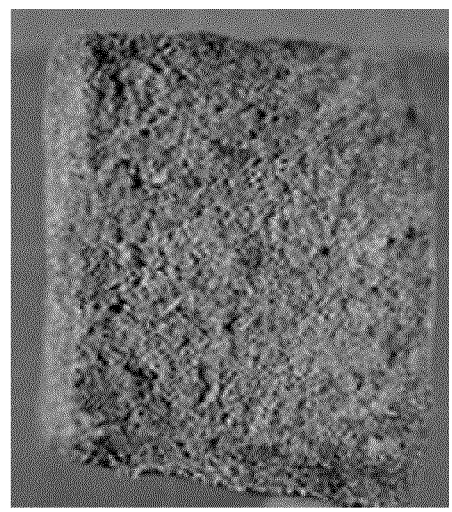
Figure 2D:
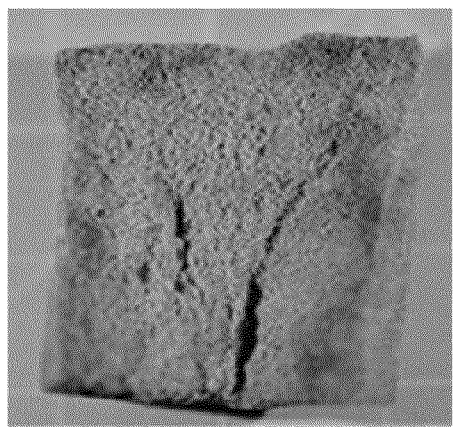

Without limitation, the majority of the systems described herein are directed to biodegradable polyester-based polyurethane foams and methods of producing same. As required, embodiments of the present disclosure are provided herein. However, the disclosed embodiments are merely exemplary, and it should be understood that the present disclosure may be embodied in many various and alternative forms.

The accompanying figures, which are not necessarily drawn to scale, and which are incorporated into and form a part of the instant specification, illustrate several aspects and embodiments of the present disclosure and, together with the description therein, serve to explain the principles of the process of producing biodegradable polyester-based polyurethane foams.

The drawings are provided only for the purpose of illustrating select embodiments of the apparatus and as an aid to understanding and are not to be construed as a definition of the limits of the present disclosure. For purposes of teaching and not limitation, the illustrated embodiments are directed to biodegradable polyester-based polyurethane foams and methods of producing same.

Definitions

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the phrase "polyester-based polyurethane foam" means that the foam is produced with at least one polyol component in the foam which is a polyester. The advantage of producing a foam with some level of polyester polyol versus a foam with no polyesters (i.e. polyether, polystyrene, polybutadiene-based foams) is that the ester linkages are more susceptible to hydrolysis which can lead to a more biodegradable foam. In addition, polyesters-based foams are known to have improved mechanical strength properties relative to polyether-based foams.

As used herein, the phrase "soil-dwelling carbon-digesting bacteria" refers to bacteria that can grow under either aerobic and/or anaerobic conditions. When not in a dormant state and under the right conditions, the bacteria break down the polyester-based polyurethane foam by first excreting an enzyme that is capable of breaking down the polymers in the foam into smaller segments at which point the bacteria can digest the smaller segments and use them as a carbon source for energy and further growth. Examples of soil-dwelling carbon-digesting bacterial include, but are not limited to, *Bacillus subtilis, Bacillus pumilus, Bacillus licheniformis, Bacillus megaterium, Bacillus cerus, Bacillus alvei, Bacillus coagulans, Bacillus simplex, Bacillus brevis*, and *Bacillus amyloliquefaciens*.

The initial breakdown of a polymer, which is the first step of the biological degradation process, can result from physical and biological forces. Physical forces such as heating/cooling, freezing/thawing, or wetting/drying can cause mechanical damage such as cracking of polymeric materials. The growth of many microorganisms can also cause small-scale swelling and bursting of polymeric materials. Most polymers are too large to pass through cellular membranes, so they must be depolymerized to smaller monomers before they can be adsorbed and degraded within microbial cells. The monomers, dimers, and oligomers of a polymer's repeating units are much easily degraded and mineralized because they can be assimilated through the cellular membrane and then further degraded by cellular enzymes. Two categories of enzymes are involved in the biological degradation of polymers: extracellular and intracellular depolymerases. During degradation, exoenzymes from microorganisms break down complex polymers, yielding smaller molecules of short chains that are small enough to pass semi-permeable outer bacterial membranes and then to be utilized as carbon energy sources. Under oxygen conditions, aerobic microorganisms are mostly responsible for the degradation of polymer. Biomass, carbon dioxide, and water are the final products of deterioration. As opposite to this, under anoxic conditions, anaerobic microorganisms play the main role in polymer destruction. The primary products are methane, water, and biomass. According to the literature microorganisms such as fungi and bacteria are involved in the degradation process of polyurethanes.

As used herein, the phrase "a carrier compound" refers to non-interactive or non-functional compound that will not interact or disrupt the function of the active ingredient with which it is blended. Its function is to act as a transport system for the active ingredient to allow for safer or easier transport and dissolution or dispersion into another medium. Non-limiting examples of the carrier compound may include Calcium carbonate, Sodium bicarbonate and Zeolite powders.

As used herein, the phrase "polyester polyol" is a polymeric material that contains ester functional groups within its backbone structure and contains 2 or more hydroxyl functionalities. Poly(ethylene adipate), which is a combination of adipic acid (diacid) and ethylene glycol (diol) is an example of a polyester polyol when terminated with ethylene glycol at both ends. The molecular structure (1) of the poly(ethylene adipate) polyol is shown below. By using starting materials with more than 2 functional acid or hydroxyl groups (triols, etc.) it is possible to produce a branched polyester polyol.

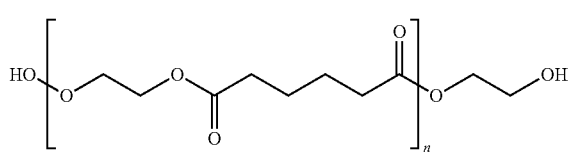

Poly(ethylene adipate)                                         (1)

As used herein, "isocyanate" refers to an organic compound with at least one isocyanate functional group with the formula R—N=C=O. The molecular structure (2) of methylene diphenyl diisocyanate containing two isocyanate functional groups, a common isocyanate used in the manufacturing of polyurethane foams is shown below.

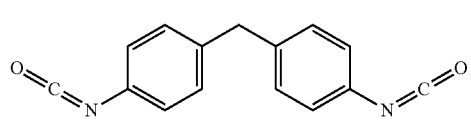

Methylene diphenyl diisocyanate                                (2)

As used herein, the "catalyst" refers to those catalysts that catalyze the reaction between an isocyanate and water and simultaneously between isocyanate and polyester polyol. Non-limiting examples of such catalysts include the family of tertiary amine catalysts, such as triethylenediamine, N-methylmorpholine, N-methylimidazole, bis(dimethylaminopropyl)amine, dimethylaminoethoxyethanol, Bis-(2-diemthylaminoethyl)-ether, dimethylaminopropylurea, N-dimethylaminopropyl-N-(2-hydroxyethyl)-N-methylamine, and N-dimethylaminoethyl-N-(2-hydroxyethyl)-N-methylamine. Another example is the family of metal-based catalysts, for example, dibutyltin dilaurate, Tin(II) 2-ethylhexanoate, bismuth neodecanoate, potassium octoate, potassium acetate, zinc carboxylates, nickel carboxylates.

Polyurethane foams are synthetic polymers that exhibit good mechanical properties, low material cost, eco-friendliness, and can be used as an alternative to solid plastics and other traditional materials. The basic structure of polyurethanes consists of (1) isocyanate (2) polyol, and (3) chain extender. Generally, a chain extender is a small molecular weight molecule containing 2 or more hydroxy groups that react with isocyanates in the same way as the polyol reacts. An isocyanate functional group reacts with hydroxyl functional group to produce a urethane linkage, where this process can be repeated to generate a polymeric chain including a combination of polyol, isocyanate and chain extender molecules. The reaction of isocyanate and polyol to form polyurethane is shown below.

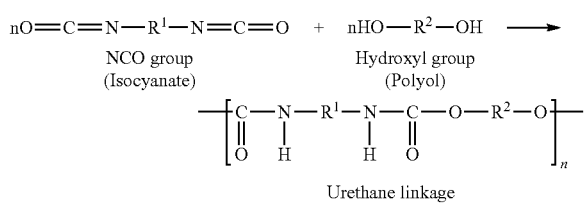

Urethane linkage

To produce a PU foam, the presence of a blowing agent is required. In this case, water is added where a reaction with an isocyanate functional group will produce a chain reaction that produces carbon dioxide gas, as shown below. An amine is produced from the initial isocyanate group, which will react with another isocyanate group to produce a urea functional group, also shown below.

(a)

R—NCO + H$_2$O + R—NHCOOH ⟶ R—NH$_2$ +
Isocyanate   Water   Carbamic acid           Amine
                                                CO$_2$ (b)

R—NCO + R—NH$_2$ ⟶ R—NHCONH—R
socyanate   Amine            Urea

These two reactions described above occur simultaneously to produce a PU foam consisting of a polymeric network containing urethane, urea, and ester functional groups in the backbone of these polymers. Additional additives such as catalysts, surfactants, emulsifiers, etc. can be added to help balance the two reactions described above to produce a stable PU foam.

To enhance the biodegradability, bacteria such as *Bacillus* species is added in powder form using a carrier solid (Zeolite or Calcium Carbonate) that evenly disperses the bacteria throughout the foam. Canadian Patent Application No. 2,828,174 entitled "Impregnated Odour Control Products and Methods of Making the Same" discloses a detailed explanation on the preparation of a solid powder containing *Bacillus* species. FIG. 1 shows a conceptual drawing of a foam block with embedded bacteria (dark spots) homogenously dispersed throughout the foam.

Synthesis

Flexible Polyester Based Polyurethane Foams

The percentage of constituents for the formulation are commonly provided in a form known as parts per hundred polyol meaning a base polyol has a mass of 100 g and all other constituents are based on this base polyol. A good example is WO patent publication: https://patents.google.com/patent/WO2018000095A1/en which is incorporated herein by reference in its entirety. Below is a list of common ingredients and their typical proportion ranges relative to the base polyol.

| | |
|---|---|
| Polyester polyol | 100 g |
| Chain extender | 2-10 g |
| Water | 0.5-10 g |
| Catalyst | 0.1-2.0 g |
| Surfactant | 0.5-3.0 g |
| Isocyanate | 20-200 g |

Optional Constituents

| | |
|---|---|
| Plasticizer | 0-30 g |
| Dye | 0-5.0 g |
| Antioxidant | 0-1.0 g |
| Flame retardant | 0-10 g |
| Emulsifier | 0-5.0 g |

Foam Formulation Specifics

The foam is produced using isocyanate having an index in the range from about 70 to about 200, and more preferably in the range from about 90 to about 115. Isocyanate index refers to the ratio of isocyanate functional groups relative to hydroxyl functional groups. An index of 100 means an exact ratio, where lower means less isocyanate relative to hydroxyl groups. The isocyanate has an average functionality in the range from 2 to 4, and more preferably 2.1 to 2.5. The polyester polyol molecular weight is in the range from about 200 to about 5000 g/mol, and preferably in the range from about 2000 to about 3000 g/mol. The polyester polyol average hydroxyl functionality is in the range from about 1.1 to about 6, and preferably between 2 to 3. The polyester polyol hydroxyl number is in the range from about 20 to about 300 mg KOH/g polyol, and preferably in the range from about 30 to about 60 mg KOH/g polyol).

Biodegradable Polyurethane Foam Properties

The resulting biodegradable polyurethane foam as produced herein is characterized by a foam density in a range from about 5 kg/m$^3$ to about 1000 kg/m$^3$, and more preferably in a range from about 20 kg/m$^3$ to about 60 kg/m$^3$. The tensile modulus is in a range from about 2 kg/cm$^2$ to about 100 kg/cm$^2$, and preferably in a range from about 10 kg/cm$^2$ to about 50 kg/cm$^2$, as per ASTM D3574-17 or ASTM D1623.

The resulting biodegradable polyurethane foam also exhibits elongation at break in the range from about 15% to about 700%, and preferably the range from about 200% to about 600% as per ASTM D3574-17 or ASTM D1623. It further exhibits a foam percent modern carbon (pMC) in the range from about 10% to about 100% (preferably 50-100%), see the following patent publication, which is incorporated herein by reference in its entirety. (https://patents.google.com/patent/US20140275305A1/en)

Table 1 shows the results from an ISO 16929 biodegradation test that determines the degree of disintegration of plastic materials in a pilot scale aerobic compost under defined conditions. Samples were placed in 80 Litre polypropylene test chambers with approximately 66 kg of inoculum. Samples were placed in a polypropylene netting with 5 mm pores mixed with 5 mm sieved compost. 1% bio-waste addition was added. The test duration was 90 days, and the temperature profile of the testing chamber over that duration was as follows: T0 (days): 63° C., T7d: 58° C., T14d: 55° C., T21d: 54° C., T28d: 46° C., T35d: 48° C., to approximately 40° C. for T90 days. FIGS. 2A, 2B, 2C and 2D show photos of foam from disintegration testing before (2A) and after an aerobic composting test (ISO 16929) (2B, 2C and 2D).

TABLE 1

Disintegration under aerobic conditions (ISO 16929).

| Sample | % Disintegration |
|---|---|
| Control Foam | 11.0 |
| Control + 0.05% bacteria in Zeolite | 17.9 |
| Control + 0.05% bacteria in Calcium carbonate | 26.7 |

Table 2 shows the results from another aerobic composting study using a modified version of ASTM D5338 for determining aerobic biodegradation of polyurethane foams containing bacteria with and without a carrier compound. Each sample was placed in a separate 1.75 Litre polyethylene test chamber with 612 g of inoculum which consisted of four layers of municipal compost (400 g in total) and two layers of food scraps (200 g in total) and was topped with a thin layer of coal fly ash (12 g). The test duration was 25 days, and the temperature of the testing chamber was 35° C. for the first two days and 58° C. for the remaining 23 days.

TABLE 2

Disintegration under aerobic conditions when using bacteria and bacteria embedded in a carrier compound.

| Sample | Normalized Disintegration (Sample/ Control Foam) |
|---|---|
| Control + 0.025% bacteria in Calcium carbonate | 1.08 |
| Control + 2.5% bacteria (no carrier) | 1.19 |
| Control + 5% bacteria (no carrier) | 1.58 |

Table 3 shows the results from a high-rate dry anaerobic batch fermentation process which was performed according to ASTM D5511. This process simulates and accelerates biodegradation process which takes place in a landfill. For each test, 15 g of the sample (milled to <1 mm) and 1 kg of stabilized highly active inoculum were added to a vessel with volume of 2.5 Litre. The incubation temperature was 52° C.±2° C. and the mixture was left to ferment batch-wise for 16 days.

TABLE 3

Biodegradation under anaerobic conditions (ASTM D5511).

| Sample | % Biodegradation |
| --- | --- |
| Industry-standard ethylene vinyl acetate (EVA) foam | 0.6 |
| Industry-standard polyether PU foam | −0.1 |
| Biodegradable polyester PU foam + 0.05% bacteria in Calcium carbonate | 12.6 |

Thus, to summarize, the present disclosure provides a biodegradable foam, comprising polyester-based polyurethane foam, and a soil-dwelling carbon-digesting bacteria or a mixture comprised of a soil-dwelling carbon-digesting bacteria embedded in a carrier compound, said mixture substantially homogenously dispersed throughout said polyester-based polyurethane foam, the bacteria-containing polyester polyurethane foam characterized in that it exhibits biodegradation rates higher than a polyester-based polyurethane foam absent the soil-dwelling carbon-digesting bacteria.

In an embodiment, the soil-dwelling carbon-digesting bacteria comprises at least one strain of the genus *Bacillus*.

In an embodiment, the soil-dwelling carbon-digesting bacteria is selected from the group consisting of *Bacillus subtilis, Bacillus pumilus, Bacillus licheniformis, Bacillus megaterium, Bacillus cerus, Bacillus alvei, Bacillus coagulans, Bacillus simplex, Bacillus brevis*, and *Bacillus amyloliquefaciens*.

In an embodiment, the carrier compound is selected from the group consisting of Calcium carbonate, Sodium Bicarbonate and Zeolite.

In an embodiment, the soil-dwelling carbon-digesting bacteria embedded in a carrier compound is present in said carrier compound, in a range from about 0.001 wt % to about 100 wt %.

In an embodiment, the soil-dwelling carbon-digesting bacteria embedded in a carrier compound is present in said polyester-based polyurethane foam, in a range from about 0.0001 to about 25.0 wt % of the total foam and preferably in a range from about 0.025 to about 10 wt %. It will be understood that by varying the amount of bacteria mixed into the PU foam facilitates fine tuning of the rate of biodegradation, with higher amounts giving faster degradation rates.

A significant advantage to the product and method disclosed herein is that the rate of biodegradation can be controlled and tuned. The desired degradation rate of the product will be determined by the use of the final foam product. For example, produced products which are highly disposable (e.g. single use products or products intended to be used only a few times—for example single use earplugs) then a higher concentration of bacteria would be used. On the other hand, products with longer lifetimes, such as midsoles for footwear would require that less bacteria would be used as the lifetime of footwear is preferably years. The control over the concentration of the bacteria in the polyurethane foam, and therefore the tunability of the biodegradation rate of the foam, is further enhanced by the feasibility of utilizing pure bacteria as well as bacteria present in a carrier compound, where pure bacteria yield significantly higher degradation rates.

In an embodiment, the particle size of the bacteria and carrier compounds are equal to or less than about 44 microns. The bacteria and calcium carbonate particles are both 44 microns where they are physically blended to obtain the desired concentration of bacteria in the mixture.

In an embodiment, the soil-dwelling carbon-digesting bacteria embedded in a carrier compound is present in said polyester-based polyurethane foam, in a range from about 0.01 to about 0.5 wt % of the total foam.

In an embodiment, the foam is characterized by a tensile modulus in a range from about 5.0 kg/cm$^2$ to about 100 kg/cm$^2$.

In an embodiment, the foam is characterized by a density in a range from about 5 kg/m$^3$ to about 1000 kg/m$^3$.

In an embodiment, the foam is characterized by an elongation at break in a range from about 15 to about 700%.

In an embodiment, the foam has a percent modern carbon in a range from about 0 to about 100%.

In an embodiment, the foam is characterized in that it has a modulus equal to or greater than 50 kg/cm$^2$.

The present disclosure also provides a method of producing a biodegradable polyurethane foam comprising mixing polyester polyol with catalysts, water and soil-dwelling carbon-digesting bacteria which are embedded in a carrier compound, to produce a mixture. The method includes mixing isocyanate into the mixture to induce a chemical reaction between the isocyanate and water to produce carbon dioxide gas, and simultaneously induce a chemical reaction between the isocyanate and polyester polyol to produce a polyester based polyurethane polymer with carbon dioxide bubbles trapped within to produce said biodegradable polyurethane foam. The biodegradable polyurethane foam is characterized in that it exhibits biodegradation rates higher than a polyester-based polyurethane foam absent the bacteria.

In an embodiment, the method further comprises adding one or more catalysts to the mixture, the catalyst being selected to catalyze the reaction between isocyanate and water and simultaneously between isocyanate and polyester polyol.

In an embodiment of the method the isocyanate is selected from the group consisting of 4,4'-Methylene diphenyl diisocyanate, 2,4-Methylene diphenyl diisocyanate, 2,2'-Methylene diphenyl diisocyanate, 2,4-Toluene diisocyanate, 2,6-Toluene diisocyanate, polymeric methylene diphenyl diisocyanate and carbodiimide-modified methylene diphenyl diisocyanate.

In an embodiment of the method the catalyst is selected from the group consisting of triethylenediamine, N-methylmorpholine, N-methylimidazole, bis(dimethylaminopropyl)amine, dimethylaminoethoxyethanol, Bis-(2-diemthylaminoethyl)-ether, dimethylaminopropylurea, N-dimethylaminopropyl-N-(2-hydroxyethyl)-N-methylamine, and N-dimethylaminoethyl-N-(2-hydroxyethyl)-N-methylamine, dibutyltin dilaurate, Tin(II) 2-ethylhexanoate bismuth neodecanoate, potassium octoate, potassium acetate, zinc carboxylates and nickel carboxylates.

In an embodiment of the method the catalyst is a tertiary amine catalyst.

In an embodiment of the method the soil-dwelling carbon-digesting bacteria comprises at least one strain of the genus *Bacillus*.

In an embodiment of the method the soil-dwelling carbon-digesting bacteria is selected from the group consisting of *Bacillus subtilis, Bacillus pumilus, Bacillus licheniformis,*

*Bacillus megaterium, Bacillus cerus, Bacillus alvei, Bacillus coagulans, Bacillus simplex, Bacillus brevis*, and *Bacillus amyloliquefaciens*.

In an embodiment of the method the carrier compound is selected from the group consisting of calcium carbonate, zeolite, and sodium bicarbonate.

In an embodiment the method further includes mixing into the mixture surfactants, plasticizers and chain extenders.

In an embodiment the method further includes mixing into said mixture flame retardants, anti-oxidants, cell openers, emulsifiers, hardening agents, non-functional fillers, cross-linking agents, dyes, pigments, or other hydroxy or amine functionalized materials.

In an embodiment the method further includes soil-dwelling carbon-digesting bacteria embedded in a carrier compound is present in the mixture in a range from about 0.001 to about 10.0 wt % of the total foam.

In an embodiment of the method the produced biodegradable polyurethane foam is characterized by having a modulus in a range from about 2 kg/cm$^2$ to about 100 kg/cm$^2$.

In an embodiment of the method the produced biodegradable polyurethane foam is characterized by having a density in a range from about 5 kg/m$^3$ to about 1000 kg/m$^3$.

In an embodiment of the method the produced biodegradable polyurethane foam is characterized by having an elongation at break in a range from about 15 to about 700%.

In an embodiment of the method the produced biodegradable polyurethane foam is characterized by having a percent modern carbon in a range from about 0 to about 100%.

In an embodiment of the method the produced biodegradable polyurethane foam is characterized by having an isocyanate index in a range from about 70 to about 200.

In an embodiment of the method the produced biodegradable polyurethane foam is characterized by having an average isocyanate functionality in a range from about 2.0 to about 6.0.

In an embodiment of the method the produced biodegradable polyurethane foam is characterized by having a polyester polyol molecular weight in a range from about 500 to about 5000 g/mol.

In an embodiment of the method the produced biodegradable polyurethane foam is characterized by having a polyester polyol average hydroxyl functionality in a range from about 1.1 to about 6.0.

In an embodiment of the method the produced biodegradable polyurethane foam is characterized by having a polyester polyol hydroxyl number in a range from about 20 to about 300 mg KOH/g polyol.

Therefore what is claimed is:

1. A biodegradable foam, comprising:
   a) polyester-based polyurethane foam; and
   b) a soil-dwelling carbon-digesting bacteria, or a mixture comprised of a soil-dwelling carbon-digesting bacteria embedded in a carrier compound, said soil-dwelling carbon-digesting bacteria or mixture substantially homogeneously dispersed throughout said polyester-based polyurethane foam, said polyester-based polyurethane foam containing said soil-dwelling carbon-digesting bacteria characterized in that it exhibits biodegradation rates higher than the same polyester-based polyurethane foam absent the soil-dwelling carbon-digesting bacteria.

2. The biodegradable foam according to claim 1, wherein said soil-dwelling carbon-digesting bacteria comprises at least one strain of the genus *Bacillus*.

3. The biodegradable foam according to claim 1, wherein said soil-dwelling carbon-digesting bacteria is *Bacillus subtilus, Bacillus pumilus, Bacillus licheniformis, Bacillus megaterium, Bacillus cerus, Bacillus alvei, Bacillus coagulans, Bacillus simplex, Bacillus brevis*, or *Bacillus amyloliquefaciens*.

4. The biodegradable foam according to claim 1, wherein said carrier compound is Calcium carbonate, Sodium Bicarbonate or Zeolite.

5. The biodegradable foam according to claim 1, wherein said soil-dwelling carbon-digesting bacteria is present in the carrier compound in an amount of at least 0.001 wt % of said mixture.

6. The biodegradable foam according to claim 1, wherein said soil-dwelling carbon-digesting bacteria embedded in a carrier compound is present in said polyester-based polyurethane foam, in a range from about 0.0001 wt % to about 25.0 wt % of the total foam.

7. The biodegradable foam according to claim 1, wherein said soil-dwelling carbon-digesting bacteria embedded in a carrier compound is present in said polyester-based polyurethane foam, in a range from about 0.01 to about 0.5 wt % of the total foam.

8. The biodegradable foam according to claim 1, characterized by a tensile modulus in a range from about 5.0 kg/cm$^2$ to about 100 kg/cm$^2$.

9. The biodegradable foam according to claim 1, characterized by a density in a range from about 5 kg/m$^3$ to about 1000 kg/m$^3$.

10. The biodegradable foam according to claim 1, characterized by an elongation at break in a range from about 15 to about 700%.

11. The biodegradable foam according to claim 1, having a percent modern carbon in a range from about 0 to about 100%.

12. The biodegradable foam as in any one of claims 1 to 11, characterized in that it has a modulus equal to or greater than 50 kg/cm$^2$.

13. A method of producing a biodegradable foam according to claim 1, comprising:
   a) mixing polyester polyol with
      i) one or more catalysts,
      ii) water and
      iii) soil-dwelling carbon-digesting bacteria, or a soil-dwelling carbon-digesting bacteria embedded in a carrier compound,
   to produce a mixture, and
   b) mixing isocyanate into said mixture to induce a chemical reaction between the isocyanate and the water to produce carbon dioxide gas, and simultaneously induce a chemical reaction between the isocyanate and the polyester polyol to produce a polyester based polyurethane polymer with carbon dioxide bubbles trapped within to produce said biodegradable polyester-based polyurethane foam, said biodegradable polyester-based polyurethane foam characterized in that it exhibits biodegradation rates which are higher than the same polyester-based polyurethane foam absent the soil-dwelling carbon-digesting bacteria.

14. The method according to claim 13, wherein said carrier compound is calcium carbonate, zeolite, or sodium bicarbonate.

15. The method according to claim 13, wherein said soil-dwelling carbon-digesting bacteria embedded in the carrier compound is present in said mixture in a range from about 0.001 to about 10.0 wt % of the total foam.

16. The method according to claim 13, wherein said isocyanate is 4,4'-Methylene diphenyl diisocyanate, 2,4-Methylene diphenyl diisocyanate, 2,2'-Methylene diphenyl diisocyanate, 2,4-Toluene diisocyanate, 2,6-Toluene diisocyanate, polymeric methylene diphenyl diisocyanate, or carbodiimide-modified methylene diphenyl diisocyanate.

17. The method according to claim 13, wherein the one or more catalysts are selected to catalyze the reaction between isocyanate and water and simultaneously between isocyanate and polyester polyol.

18. The method according to claim 13, wherein said one or more catalysts are a tertiary amine catalyst.

19. The method according to claim 13, wherein said one or more catalysts are triethylenediamine, N-methylmorpholine, N-methylimidazole, bis(dimethylaminopropyl)amine, dimethylaminoethoxyethanol, Bis-(2-diemthylaminoethyl)-ether, dimethylaminopropylurea, N-dimethylaminopropyl-N-(2-hydroxyethyl)-N-methylamine, or N-dimethylaminoethyl-N-(2-hydroxyethyl)-N-methylamine.

20. The method according to claim 13, wherein said one or more catalysts are dibutyltin dilaurate, Tin(II) 2-ethylhexanoate bismuth neodecanoate, potassium octoate, potassium acetate, zinc carboxylates, or nickel carboxylates.

21. The method according to claim 13, wherein said soil-dwelling carbon-digesting bacteria comprises at least one strain of the genus *Bacillus*.

22. The method according to claim 13, wherein said soil-dwelling carbon-digesting bacteria is *Bacillus subtilus, Bacillus pumilus, Bacillus licheniformis, Bacillus megaterium, Bacillus cerus, Bacillus alvei, Bacillus coagulans, Bacillus simplex, Bacillus brevis*, or *Bacillus amyloliquefaciens*.

23. The method according to claim 13, further including mixing into said mixture surfactants, plasticizers and chain extenders.

24. The method according to claim 13, further including mixing into said mixture flame retardants, anti-oxidants, cell openers, emulsifiers, hardening agents, non-functional fillers, cross-linking agents, dyes, pigments, or other hydroxy or amine functionalized materials.

25. The method according to claim 13, wherein said biodegradable polyurethane foam is characterized by having a modulus in a range from about 2 $kg/cm^2$ to about 100 $kg/cm^2$.

26. The method according to claim 13, wherein said biodegradable polyurethane foam is characterized by having a density in a range from about 5 $kg/m^3$ to about 1000 $kg/m^3$.

27. The method according to claim 13, wherein said biodegradable polyurethane foam is characterized by having an elongation at break in a range from about 15 to about 700%.

28. The method according to claim 13, wherein said biodegradable polyurethane foam is characterized by having a percent modern carbon in a range from about 0 to about 100%.

29. The method according to claim 13, wherein said biodegradable polyurethane foam is characterized by having an isocyanate index in a range from about 70 to about 200.

30. The method according to claim 13, wherein said biodegradable polyurethane foam is characterized by having an average isocyanate functionality in a range from about 2.0 to about 6.0.

31. The method according to claim 13, wherein said biodegradable polyurethane foam is characterized by having a polyester polyol molecular weight in a range from about 500 to about 5000 g/mol.

32. The method according to claim 13, wherein said biodegradable polyurethane foam is characterized by having a polyester polyol average hydroxyl functionality in a range from about 1.1 to about 6.0.

33. The method according to claim 13, wherein said biodegradable polyurethane foam is characterized by having a polyester polyol hydroxyl number in a range from about 20 to about 300 mg KOH/g polyol.

\* \* \* \* \*